United States Patent [19]

Chiarino et al.

[11] Patent Number: 4,902,688
[45] Date of Patent: Feb. 20, 1990

[54] 4-(3-COUMARINYL)-THIAZOLE-DERIVATIVES WITH ANTI-ALLERGIC, ANTI-ANAPHYLACTIC AND ANTI-ARTHRITIC ACTIVITY AND COMPOSITIONS CONTAINING THEM

[75] Inventors: Dario Chiarino, Monza; Gian Carlo Grancini, Nova Milanese; Viviana Frigeni, Monza; Angelo Carenzi, Busto Arsizio, all of Italy

[73] Assignee: Zambon Group S.p.A., Vicenza, Italy

[21] Appl. No.: 172,230

[22] Filed: Mar. 23, 1988

[30] Foreign Application Priority Data

Mar. 25, 1987 [IT] Italy ................ 19846 A/87

[51] Int. Cl.⁴ ................ A61K 31/495; A61K 31/425; C07D 417/04; C07D 417/14
[52] U.S. Cl. ................ 514/253; 514/320; 514/371; 544/367; 546/196; 548/194; 548/195
[58] Field of Search ........ 548/195; 544/367; 546/196; 514/371, 253, 320

[56] References Cited

U.S. PATENT DOCUMENTS

| | | | |
|---|---|---|---|
| 4,238,496 | 12/1980 | Hess et al. | 548/195 |
| 4,246,271 | 1/1981 | Cousse et al. | 548/195 |
| 4,404,389 | 9/1983 | Vamvakaris et al. | 544/367 |
| 4,407,810 | 10/1983 | Eilingsfled et al. | 548/195 |
| 4,701,456 | 10/1987 | Dewald et al. | 514/253 |
| 4,766,137 | 8/1988 | Carenzi et al. | 514/371 |
| 4,766,138 | 8/1988 | Carenzi et al. | 548/195 |

FOREIGN PATENT DOCUMENTS 35186  3/1983  Japan ................ 548/196

OTHER PUBLICATIONS

Rajeswar et al., Chemical Abstracts, vol. 106, No. 196413 (1987).
Gursoy et al., Chemical Abstracts, vol. 99, No. 175646 (1983).

Primary Examiner—Mukund J. Shah
Assistant Examiner—E. Bernhardt
Attorney, Agent, or Firm—Stevens, Davis, Miller & Mosher

[57] ABSTRACT

Compounds of formula

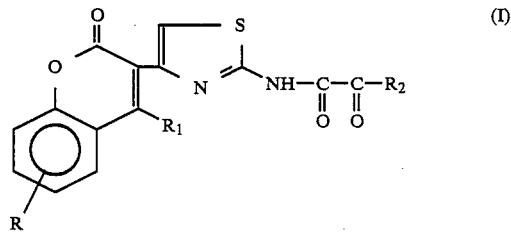

(wherein R, $R_1$ and $R_2$ have the meanings reported in the specification) and their preparation are described.

The compounds of formula I have anti-allergic, anti-anaphylactic and anti-arthritic activity and are useful in pharmaceutical field.

Compositions for pharmaceutical use containing a compound of formula I as active ingredient are described too.

8 Claims, No Drawings

4-(3-COUMARINYL)-THIAZOLE-DERIVATIVES WITH ANTI-ALLERGIC, ANTI-ANAPHYLACTIC AND ANTI-ARTHRITIC ACTIVITY AND COMPOSITIONS CONTAINING THEM

The present invention relates to compounds with anti-allergic, anti-anaphylactic and anti-arthritic activity and, more particularly, relates to derivatives of 2-thiazolyl-oxamic acid, their preparation and their use in pharmaceutical field.

The compound known as Cromolyn (Merck Index 10th Ed. No. 2580, page 371) or as disodium cromoglycate (described in U.K. Patent No. 1.144.906-Fisons) has the characteristic of preventing the release of the autocoids formed during allergic reactions and induced by antigen-antibody interactions.

For this characteristic disodium cromoglycate is used in therapy as anti-allergic drug especially in asthmatic diseases.

However said compound is not adsorbed after oral administration and this disadvantage limits its application considerably.

In order to attempt to overcome this disadvantage many other compounds were prepared which modified little by little the structure of disodium cromoglycate so that compounds structurally and chemically different from the parent compound were obtained. Among these compounds the derivatives of phenyloxamic acid [J. Med. Chem., 21(9), 930, (1978)] and of 4-aryl-2-thiazolyl-oxamic acid (U.K. Patent Application No. 2.023.580-Boehringer Ingelheim and European Patent No. 44442-BASF) may be cited.

We have now found and they are the object of the present invention, compounds of formula

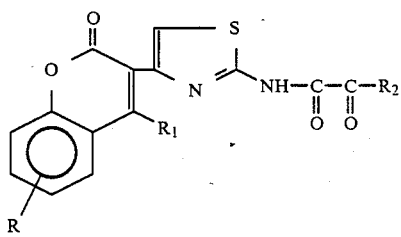

(I)

wherein
R and $R_1$, which are the same or different, represent hydroxy, a hydrogen or a halogen atom, a $C_1$-$C_4$ alkyl or alkoxy;
$R_2$ represents hydroxy, an $OR_3$ group or a

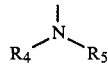

group;
$R_3$ represents a $C_1$-$C_6$ alkyl, a benzyl, a group of formula —$(CH_2$—$CH_2$—$O)_n$—$R_6$ where n represents an integer from 1 to 4 and $R_6$ represents a hydrogen atom or a $C_1$-$C_4$ alkyl;
$R_4$ and $R_5$, which are the same or different, represent a hydrogen atom, a $C_1$-$C_4$ alkyl, a benzyl, a phenyl, or $R_4$ and $R_5$, together with the nitrogen atom to which they are bonded, form a 1-piperidinyl, 1-piperazinyl, 4-methyl-1-piperazinyl radical.

Furthermore, object of the present invention are the salts of the compounds of formula I wherein $R_2$ represents hydroxy, with nontoxic organic or inorganic bases suitable for pharmaceutical use and the salts of the compounds of formula I wherein $R_2$ contains a basic function, with non-toxic organic or inorganic acids suitable for pharmaceutical use.

Specific examples of said bases are sodium, potassium or calcium hydroxide, methylamine, isopropylamine, hexylamine, diethylamine, ethanolamine, 2-hydroxymethyl-2-amino-1,3-propanediol, glycine, alanine, valine, leucine, isoleucine, serine, threonine, aspartic acid, glutamic acid, arginine, lysine, cystine, cysteine, methionine, phenylalanine, tyrosine, tryptophan and histidine.

Examples of suitable acids are hydrochloric or hydrobromic acid, benzoic acid, 4-hydroxybenzoic acid, citric acid, tartaric acid and succinic acid.

If it is not otherwise specified, the radicals representing the meanings of the substituents in general formula I are preferably:
alkyl=linear or branched $C_1$-$C_4$ alkyl,
alkoxy=$C_1$-$C_4$ alkoxy,
alkoxycarbonyl=alkoxycarbonyl having from 1 to 4 carbon atoms in the alkoxy portion,
halogen=fluorine, chlorine, bromine or iodine atom.

Examples of compounds comprised in formula I are the followings:

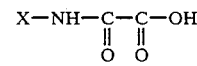

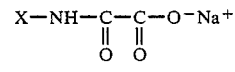

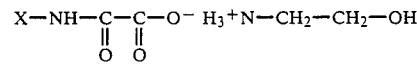

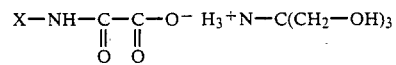

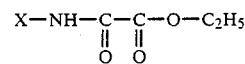

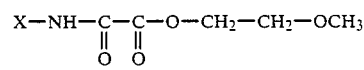

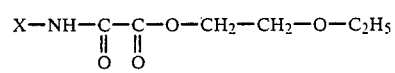

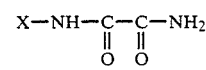

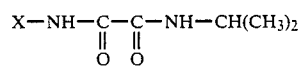

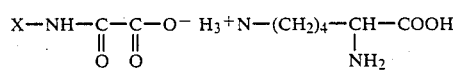

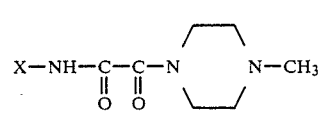

wherein X represent the group

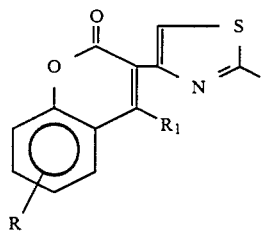

and wherein R and $R_1$ have the same above reported meanings but preferably they represent a hydrogen atom, a chlorine or bromine atom, hydroxy, a methoxy or ethoxy group.

Preferred meanings of $R_4$ and $R_5$, the same or different, are hydrogen, methyl or ethyl or $R_4$ and $R_5$, together with the nitrogen atom to which they are bonded, are a 1-piperidinyl, 1-piperazinyl or 4-methyl-1-piperazinyl radical.

The compounds of formula I are endowed with anti-allergic, anti-anaphylactic and anti-arthritic activity and they can be used in pharmaceutical field.

The preparation of the compounds of formula I is carried out by using methods already known in organic chemistry.

Useful starting materials are the compounds of formula

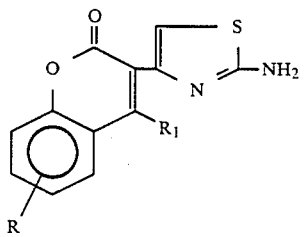
(II)

(wherein R and $R_1$ have the above reported meanings) 2-amino-4-(3-coumarinyl)-thiazoles of formula II are known compounds [C. F. Koelsch, J. Am. Chem. Soc. 72, 2993 (1950); M. Trkovnik et al., Org. Prep. and Proced. Int. 10, 215 (1978)] or they can be easily prepared from the corresponding 3-acetyl-coumarine (2H-1-benzopyran-2-one) by bromination and condensation of the so obtained alfa-bromo-ketone with thiourea.

The reaction of the compounds of formula II with derivatives of oxalic acid of formula

(III)

(wherein $R_3$ has the above reported meanings) carried out in the presence of an organic or inorganic base and of a solvent that may be the organic base itself, gives the esters of formula I ($R_2=OR_3$).

From these esters, the other compounds of formula I are prepared by means of known reactions.

For instance, the hydrolysis of the esters of formula I wherein $R_2=OR_3$ gives the corresponding acids ($R_2=OH$) which, if desired, can be salified by reaction with a pharmaceutically acceptable base.

The reaction of the compounds of formula I wherein $R_2=OR_3$, with ammonia or with a suitable amine gives the compounds of formula I wherein $R_2=NH_2$ or $R_2 =$ 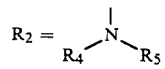

respectively.

Such compounds, in case they contain basic groups, can be salified, then, by reaction with a pharmaceutically acceptable acid. Other esters of formula I can be prepared by means of known methods from the acids as well as by transesterification.

The compounds object of the present invention have interesting anti-allergic, anti-anaphylactic and anti-arthritic properties.

The compounds of this invention are more active than known compounds such as diisodium cromoglycate, however the anti-allergic and anti-anaphylactic activity is particularly remarkable in the compounds of formula I wherein $R_2$ is hydroxy or an $OR_3$ group. On the other hand the compounds of formula I wherein $R_2$ is a

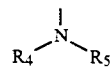

group are particularly preferred as far as their anti-arthritic activity is concerned.

ANTI-ALLERGIC AND ANTI-ANAPHYLACTIC ACTIVITY

With reference to the anti-allergic and anti-anaphylactic properties, the pharmacological screening carried out on the compounds of formula I showed that they are endowed with the property of interfering with the appearance of the allergic pathology experimentally induced in the experimental animal. This interference resulted to be remarkable and highly selective.

In the experimental animal, after treatment with the compounds of this invention with even large dosages, no important variations were recorded in the principal regulatory functions studied, such as for example the cardiocircolatory and the respiratory functions.

Besides, the coordination functions peculiar to the central nervous system were not influenced and no effect of excitatory or sedative type appeared.

Finally, neither in vitro nor in vivo any direct antagonistic pharmacological action towards humoral and tissue autocoids known in allergic pathology, such as histamine, serotonin, bradykinin and SRS-A was noted.

The pharmacological action of the compounds of this invention was shown by a dual series of indipendent experiments in which:

(a) a passive cutaneous anaphylaxis experimental model;
(b) an experimental model of systemic sensibilization appropriate for the appearance of bronchoconstriction by inhalation of the specific antigen;

was induced in the experimental animals.

The first test was performed in the rat in accordance with Goose J. and Blair A.M.J.N. [Immunology, 16, 749, (1969)] and Binaghi R. A. and Benacerraf B. [J. Immol., 92, 920, (1964)]; the production of the hemocytotropic serum necessary for the accomplishment of the test was obtained according to the method set forth by Mota I. [Immunology, 7, 681, (1964)].

The second test was accomplished on guinea-pig, sensitized for 4-5 weeks by parenteral administration of ovalbumin as allergen and adjuvant. The trigger reaction was induced following aerosol inhalation of the allergen until appearance of the characteristic signs of bronchoconstriction.

In these two tests the specific inhibitory activity of the compounds of this invention proved to be dose-dependent and clearly reproducible by the three selected administration ways: oral, peritoneal (i.p.) and venous (i.v.).

For example, $ED_{50}$ value obtained in the passive cutaneous anaphylaxis test in rat is 0.3 mg/kg/i.p. for N-[4-(3-coumarinyl)-2-thiazolyl]oxamate of L-lysine.

In the same experiments known reference compounds gave the following results:
4-phenyl-thiazole oxamic acid $ED_{50}=3.5$ mg/kg/i.p.
4-(4-methoxyphenyl)-thiazole oxamic acid $ED_{50}=2.6$ mg/kg/i.p.
4-(2-furyl)-thiazole oxamic acid $ED_{50}=3.2$ mg/kg/i.p.

ANTI-ARTHRITIC ACTIVITY

Anti-arthritic activity was evaluated using the test for Freund experimental arthritis induced in the rat by a subplantar injection of a 0.5% solution of killed Butyricum mycobacteria in paraffin oil as described by Newbould B. B. (Brit. J. Pharmacol., 1963, 21, 127).

Compounds found to be active in Freund's experimental arthritis were shown to have considerable clinical usefulness in the treatment of rheumatoid arthritis.

The experimental model of Freund's arthritis used for the pharmacological investigation of the compounds of this invention makes it possible not only to evaluate the pharmacological activity but to acquire indications on the mechanism of the action of the tested compounds.

In this experimental model, in fact, two stages may be considered: the stage sustained predominantly by a specific inflammatory mechanism (primary stage) and the stage sustained principally by an immunity mechanism (secondary stage).

The pharmacological investigation of the compound of this invention was carried out by administering peritoneally to the experimental animal a dosage of 0.06 mmol/Kg/day for a period of 21 consecutive days beginning the day before innoculation of the mycobacteria.

The pharmacological activity was measured by determining both the velocity of erythrosedimentation (VES) and the change in volume of the hind limbs.

The limb which was the seat of the innoculation represents the primary stage while the contra-lateral limb, where the onset of the pathological process takes place about the 12th day after innoculation, represents the secondary stage.

Treatment of the mycobacteria-innoculated animals, for example with N-[4-(3-coumarinyl)-2-thiazolyl]oxamide led to a 54% inhibition of VES and to a 64% inhibition of volume growth in the contra-lateral limb (secondary stage).

The compound known as Cromolyn did not show any anti-arthritic activity in the same test.

Treatment with N-[4-(4-hydroxycoumarin-3-yl)-2-thiazolyl]oxamide led to a 83% inhibition of volume growth in secondary stage. The ratio between pharmacological dose and tolerated dose proved to be highly favourable in all the compounds for the anti-allergic and anti-anaphylactic activity as well as for anti-arthritic activity. Suitable therapeutic doses can be considered between the range from 5 to 500 mg/day depending on the formulation.

The therapeutic uses of the compounds of the present invention are in the treatment of the syndromes which accompany the arthritic and rheumatic processes and in the treatment of anaphylaxis reactions and of other various pathological syndromes having a recognized allergic nature, with localization either in the upper respiratory tracts such as, for example, hay fever and bronchial asthma, or in the cutaneous tissues and in superficial mucous membranes such as, for example, urticaria, dermatitis eczematoides, itching and allergic conjunctivitis.

Another object of the present invention are the pharmaceutical compositions containing the compounds of formula I or the pharmaceutically acceptable salts thereof as active ingredient.

These compositions can contain the active ingredient together with a pharmaceutically acceptable carrier which may be a solid or liquid, organic or inorganic pharmaceutical excipient and they are suitable for topical, oral, parenteral and rectal administration or for inhalation.

The pharmaceutical preparations can be solid, such as for example tablets, pills, capsules, powders, granules, suppositories, or liquid such as for example solutions, suspensions, emulsions, or semiliquids such as creams and ointments.

They can be also prepared in such a way that the release of the drug after administration is prolonged.

In addition to the excipients they may contain preservatives, stabilizing agents, wetting agents, emulsifying agents, salts to regulate osmotic pressure, buffers, colouring agents and flavouring agents.

They are prepared according to known methods and also contain other compatible therapeutic ingredients.

In order to better illustrate the present invention the following examples are now given.

EXAMPLE 1

Preparation of 2-ethoxy-ethyl N-[4-(3-coumarinyl)-2-thiazolyl]oxamate

To a mixture of 2-amino-4-(3-coumarinyl)-thiazole (15.4 g; 63 mmols) and of triethylamine (7.34 g; 72.5 mmols) in pyridine (115 ml), kept under stirring at the temperature of 5° C., 2-ethoxy-ethyl-oxalylchloride (13.1 g; 72.5 mmols) was added dropwise. At the end of the addition, the reaction mixture was kept under stirring for a night at room temperature and, then, was poured onto ice (230 g); it was acidified with concentrated hydrochloric acid and extracted with dichloromethane.

The organic extract was washed with water, dried on sodium sulphate and evaporated.

A solid (24.6 g) was obtained and crystallized from acetonitrile (320 ml) giving 22.9 g (93.5% yield) of the desired compound with m.p. 156°-157° C.

I.R. (KBr): significative bands at 1730, 1715, 1590, 1540 (cm$^{-1}$).

EXAMPLE 2

Preparation of 2-ethoxy-ethyl N-[4-(4-hydroxycoumarin-3-yl)-2-thiazolyl]oxamate

To a suspension of 2-amino-4-(4-hydroxycoumarin-3-yl)-thiazole (3.9 g; 15 mmols) in pyridine (40 ml), kept under stirring at the temperature of 5° C., 2 -ethoxyethyl-oxalylchloride (3.11 g; 17.25 mmols) was added dropwise.

At the end of the addition, the reaction mixture was kept under stirring at room temperature for a night and, then, poured into water and ice (80 g). A precipitate formed and it was filtered, suspended in diluted hydrochloric acid, filtered again and washed some times with water till negative halide test.

5.5 g of a solid were obtained and dissolved in dimethylformamide (200 ml) heating (external bath).

After cooling at 0° C. the precipitate (4.1 g) was filtered, suspended and kept under stirring in warm acetonitrile (100 ml).

After filtration 4 g (65.9% yield) of 2-ethoxyethyl N-[4-(4-hydroxycoumarin-3-yl)-2-thiazolyl]oxamate were obtained with m.p. 266°–268° C. (dec.).

I.R. (KBr): significative bands at 1735, 1700, 1610, 1555, 1410 (cm$^{-1}$).

EXAMPLE 3

Preparation of 2-ethoxyethyl N-[4-(7-hydroxycoumarin-3-yl)-2-thiazoly]oxamate

To a suspension of 2-amino-4-(7-hydroxycoumarin-3-yl)-thiazole (5.1 g; 19.6 mmols) [p.f. 252°–254° C.—prepared according to the method described in J. Ann. Chem. Soc. 72, 2993 (1950)] in pyridine (51 ml), kept under stirring at the temperature of 5° C., 2-ethoxy-ethyl-oxalylchloride (8.14 g; 45.1 mmols) was added dropwise.

At the end of the addition, the mixture was kept under stirring at room temperature for a night and, then, poured into water and ice (150 g). It was kept under stirring for 1.5 hours and then the precipitate was filtered.

The solid was suspended in mixture of pyridine (150 ml) and water (50 ml) and the suspension was kept under stirring for 3.5 hours. After filtration and drying a solid (5.6 g) was obtained and suspended again in warm acetonitrile (100 ml).

By filtration the desired compound (5.1 g; 64.4% yield), crystalline solid with m.p. 217°–218° C., was obtained.

I.R. (KBr): significative bands at 1732, 1700, 1610, 1570, 1540, 1380 (cm$^{-1}$).

EXAMPLE 4

Preparation of N-[4-(3-coumarinyl)-2-thiazolyl]oxamate of L-lysine dihydrate

A suspension of 2-ethoxy-ethyl N-[4-(3-coumarinyl)-2-thiazolyl]oxamate (6 g; 15.45 mmols), prepared as described in example 1, in NaOH 0.1N (232 ml) was kept at 40° C. under stirring for 45 minutes. The reaction mixture was cooled to room temperature and filtered. The solid was dissolved in trifluoroacetic acid (40 ml) and reprecipitated with water (200 ml).

The water of crystallization were acidified with hydrochloric acid at 10% till precipitation.

Both the precipitates were filtered together and washed til neutral pH and negative answer to halide test.

After drying 4.8 g of N-[4-(3-coumarinyl)-2-thiazolyl]oxamic acid were obtained and suspended in methanol at 65% (150 ml).

L-lysine (2.44 g; 16.69 mmols) was added and the suspension was heated to boiling temperature till complete solubilization. By cooling at 0° C. a precipitate was obtained and filtered giving 4.6 g (59.7% yield) of the desired compound, crystalline solid with m.p. 203°–204° C. (dec.).

I.R. (KBr): significance bands at 1715, 1680, 1605, 1540 (cm$^{-1}$).

EXAMPLE 5

Preparation of N-[4-(3-coumarinyl)-2-thiazolyl]oxamide

A suspension of 2-ethoxy-ethyl N-[4-(3-coumarinyl)-2-thiazolyl]oxamate (8 g; 20.6 mmols), prepared as described in example 1, in a solution (115 ml) of ammonia at 16% in methanol was kept under stirring for a night at room temperature.

Then the solvent was evaporated and the solid residue (6.2 g) was crystallized from acetic acid.

5.5 g (84.7% yield) of N-[4-(3-coumarinyl)-2-thiazolyl]oxamide with m.p. 297°–300° C. were obtained.

I.R. (KBr): significative bands at 1700, 1605, 1545, 1380 (cm$^{-1}$).

By working in a similar way the following compounds were prepared:

N-[4-(4-hydroxycoumarin-3-yl)-2-thiazolyl]oxamide, 81.4% yield—p.f. 330° C. (dec.).

I.R. (KBr): significative bands at 1680, 1615, 1560, 1410 (cm$^{-1}$).

N-[4-(7-hydroxycoumarin-3-yl)-2-thiazolyl]oxamide, 73% yield—m.p. 300° C. (dec.).

I.R. (KBr): significative bands at 1700, 1610, 1545, 1380 (cm$^{-1}$).

EXAMPLE 6

(1) Granules containing N-[4-(3-coumarinyl)-2-thiazolyl]oxamate of L-lysine

A mixture of 100 g of active ingredient, 155 g of lactose, 140 g of corn starch and 80 g of crystalline cellulose was stirred and the mixture was kneaded and granulated with a solution of 20 g of hydroxypropylcellulose in 400 ml of water and dried at 50° C. for 1 hour; then it was passed through a 12 mesh screen to obtain granules which were dried at 50° C. for 10 hours.

(2) Suppository containing 2-ethoxyethyl N-[4-(3-coumarinyl)-2-thiazolyl]oxamate A mixture of 5 or 15 g of active ingredient and 180 g of Witepsol (R) W-35 was heated and molten at 60° C. and the melt was cast into models so that the weight of each suppository was 1.5 g or 3 g respectively. The cast melt was cooled and solidified to obtain suppositories.

(3) Tablets containing N-[4-(4-hydroxycoumarin-3-yl)-2-thiazolyl]oxamide

A mixture of 100 g of active ingredient, 80 g of lactose, 70 g of corn starch and 40 g of crystalline cellulose was granulated in the conventional way.

The granulates was mixed with 4 g of magnesium stearate and formed into tablet each having a weight of 200 mg by a tabletting machine.

(4) Capsules containing N-[4-(7-hydroxycoumarin-3-yl)-2-thiazolyl]oxamide

A mixture of 100 g of active ingredient, 100 g of lactose, 60 g of corn starch, 40 g of crystalline cellulose and 6 g of magnesium stearate was mixed and filled into hard capsules in an amount of 200 mg for capsule by using an encapsulating machine.

(5) Ampoules (injection solution) containing
N-[4-(3-coumarinyl)-2-thiazolyl]oxamate of L-lysine The active ingredient (10 parts by weight), 2 parts by weight of sodium pyrosulfite, 1 part by weight of disodium salt of ethylenediamine-tetraacetic acid, 17 parts by weight of sodium chloride are dissolved in a sufficient quantity of water and brought to 2000 parts by weight with double distilled water. The solution was filtered and filled into 1 ml ampoules and the ampoules were sealed and sterilized.

Each ampoule contains 5 mg of active ingredient.

(6) Inhalation Aereosol Preparation containing
N-[4-(3-coumarinyl)-2-thiazolyl]oxamide The active ingredient (1 to 20 parts), soya lecithin (0.20 to 4 parts) and mixture of propellant gases (Freon 11, 12 and 14) up to 100 parts was filled into aerosol containers with metering valve. The single dose can be adjusted to provide 1 to 20 mg of active substance.

What we claim is:

1. A compound of formula

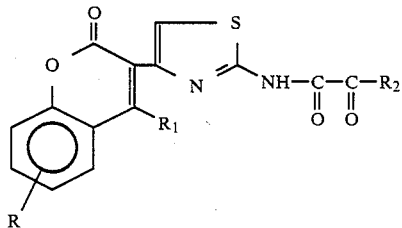

(I)

wherein

R and $R_1$ represent hydroxy, a hydrogen or a halogen atom, a $C_1$–$C_4$ alkyl or alkoxy;

$R_2$ represents hydroxy, an $OR_3$ or a

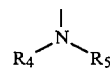

$R_3$ represents a $C_1$–$C_6$ alkyl, a benzyl, a group of formula —$(CH_2$—$CH_2$—$O)_n$—$R_6$ wherein n represents an integer from 1 to 4 and $R_6$ represents a hydrogen atom or a $C_1$–$C_4$ alkyl;

$R_4$ and $R_5$, which are the same or different, represent a hydrogen atom, a $C_1$–$C_4$ alkyl, a benzyl, a phenyl, or $R_4$ and $R_5$ together with the nitrogen atom to which they are bonded, form a 1-piperidinyl, 1-piperazinyl, 4-methyl-1-piperazinyl radical;

and salts thereof with pharmaceutically acceptable acids or bases.

2. A compound, according to claim 1, wherein R and $R_1$ represent a hydrogen, a chlorine or bromine atom, hydroxy, methoxy or ethoxy.

3. A compound according to claim 1, wherein $R_2$ represents an $OR_3$.

4. A compound according to claim 1, wherein $R_2$ represents hydroxy and salts thereof with non-toxic organic or inorganic bases suitable for pharmaceutical use.

5. A compound according to claim 1, wherein $R_2$ represents a

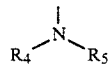

6. A compound according to claim 1, wherein $R_4$ and $R_5$, the same or different, represent hydrogen, methyl or ethyl or together with the nitrogen atom to which they are bonded form a 1-piperidinyl, 1-piperazinyl or 4-methyl-1-piperazinyl radical.

7. A pharmaceutical composition according to claim 1, for the treatment of allergic and anaphylactic diseases containing a therapeutically effective amount of a compound according to claim 1, with a pharmaceutically acceptable carrier.

8. A pharmaceutical composition according to claim 1, for the treatment of arthritis containing a therapeutically effective amount of a compound according to claim 1, with a pharmaceutically acceptable carrier.

* * * * *